(12) United States Patent
Lu et al.

(10) Patent No.: US 7,999,949 B2
(45) Date of Patent: Aug. 16, 2011

(54) SPECTROSCOPIC ELLIPSOMETERS

(75) Inventors: Tongxin Lu, San Jose, CA (US);
Xiaohan Wang, Alameda, CA (US)

(73) Assignee: Raintree Scientific Instruments (Shanghai) Corporation, Shanghai (CN)

( * ) Notice: Subject to any disclaimer, the term of this patent is extended or adjusted under 35 U.S.C. 154(b) by 0 days.

(21) Appl. No.: 11/739,679

(22) Filed: Apr. 24, 2007

(65) Prior Publication Data

US 2007/0247624 A1    Oct. 25, 2007

Related U.S. Application Data

(63) Continuation-in-part of application No. 11/735,979, filed on Apr. 16, 2007, now abandoned.

(60) Provisional application No. 60/793,926, filed on Apr. 24, 2006.

(51) Int. Cl.
*G01B 11/30* (2006.01)

(52) U.S. Cl. .............. 356/601; 356/237.1; 356/239.5; 356/367

(58) Field of Classification Search .... 356/237.1–237.6, 356/239.3, 239.5, 239.7, 239.8, 364–370
See application file for complete search history.

(56) References Cited

U.S. PATENT DOCUMENTS

| | | | | |
|---|---|---|---|---|
| 6,169,601 B1 * | 1/2001 | Eremin et al. | ............. | 356/239.8 |
| 6,987,568 B2 * | 1/2006 | Dana | ............. | 356/446 |
| 7,119,897 B2 * | 10/2006 | Vaez-Iravani et al. | ..... | 356/237.4 |
| 7,139,083 B2 * | 11/2006 | Fielden et al. | ................ | 356/630 |

* cited by examiner

*Primary Examiner* — Gregory J Toatley
*Assistant Examiner* — Iyabo S Alli
(74) *Attorney, Agent, or Firm* — Venture Pacific Law, PC

(57) ABSTRACT

The present invention discloses an optical measurement and/or inspection device that, in one application, may be used for inspection of semiconductor devices. A method is disclosed for extracting information of a device-under-test for an ellipsometer, comprising the steps: providing a plurality of incoming polarized beams using a plurality of polarizers, where each of the beams being polarized at a designated polarizing angle; using a parabolic reflector to focus said plurality of incoming polarized beams on a spot on a DUT; using a parabolic reflector to collect a plurality of beams reflected from said DUT; and analyzing said collected beams using a plurality of analyzers, wherein each of the analyzers having a designated polarizing angle with respect to its respective polarizer.

16 Claims, 8 Drawing Sheets

US 7,999,949 B2

SPECTROSCOPIC ELLIPSOMETERS

PRIORITY CLAIM

This application claims priority from a provisional patent application entitled "Spectroscopic Ellipsometer Without Moving Parts" filed on Apr. 24, 2006, having an application No. 60/793,926. This application further claims priority from a non-provisional patent application entitled "Optical Focusing Devices" filed on Apr. 16, 2007, having an application Ser. No. 11/735,979. These applications are incorporated herein by reference in its entirety.

FIELD OF INVENTION

The present invention relates to the inspection and measurement systems, and in particular, to optical inspection and measurement of devices under test such as semiconductor devices and/or wafers.

BACKGROUND

Spectroscopic ellipsometry is a very power optical measurement technology widely used in semiconductor manufacturing, optical coating and material analysis. The ellipsometer measures the complex ratio of reflectivity of Rp and Rs, where Rp is the reflectivity of the electrical field whose direction is in the plane of incidence and Rs is the reflectivity of the electrical field whose direction is perpendicular to the plane of incidence. Both Rp and Rs are complex number and they are wavelength dependent.

The ellipsometric quantities are defined as:

$$\frac{R_p}{R_s} = \left|\frac{R_p}{R_s}\right| \cdot \exp i(\delta_p - \delta_s) = \tan(\Psi) \cdot \exp i\Delta$$

where $$\tan(\Psi) = \left|\frac{R_p}{R_s}\right|$$

and $$\Delta = \delta_p - \delta_s$$

$\delta_p$ and $\delta_s$ are the phases of $R_p$ and $R_s$.

In conventional ellipsometer, in measuring the ellipsometric quantities, i.e. $\Psi$ and $\Delta$, it is necessary to rotate one of the polarizing components (the polarizer, analyzer or compensator) in the system. This limits the speed of the measurement. In some applications, it is desirable to perform measurements for a very small area (such as measuring the thin film thickness on semiconductor wafers). It is necessary to focus the light to a very small area.

Therefore, it is desirable to have spectroscopic ellipsometers capable of focusing on a small focus spot. It is further desirable to have an ellipsometer with minimal moving parts such that measurements can be taken without moving any mechanical parts in the system.

SUMMARY OF THE INVENTION

An object of the present invention is to provide methods and devices for an ellipsometer that can focus on small focus spots.

Another object of this invention is to provide methods and devices for an ellipsometer that can simultaneously polarize, reflect, analyze, and detect several rays.

Another object of this invention is to provide methods and devices for an ellipsometer that can simultaneously polarize, reflect, analyze, and detect several rays without any mechanical moving parts.

Briefly, a method for extracting information of a device-under-test for an ellipsometer, comprising the steps of providing a plurality of incoming polarized beams using a plurality of polarizers, where each of the beams being polarized at a designated polarizing angle; using a parabolic reflector to focus said plurality of incoming polarized beams on a spot on a DUT; using a parabolic reflector to collect a plurality of beams reflected from said DUT; and analyzing said collected beams using a plurality of analyzers, wherein each of the analyzers having a designated polarizing angle with respect to its respective polarizer.

An advantage of the present invention is that it provides methods and devices for an ellipsometer that can focus on small focus spots.

Another advantage of this invention is that it provides methods and devices for an ellipsometer that can simultaneously polarize, reflect, analyze, and detect several rays.

Another advantage of this invention is that it provides methods and devices for an ellipsometer that can simultaneously polarize, reflect, analyze, and detect several rays without any mechanical moving parts.

DRAWINGS

The following are further descriptions of the invention with reference to figures and examples of their applications.

DETAILED DESCRIPTIONS OF THE PREFERRED EMBODIMENTS

Figure 1:
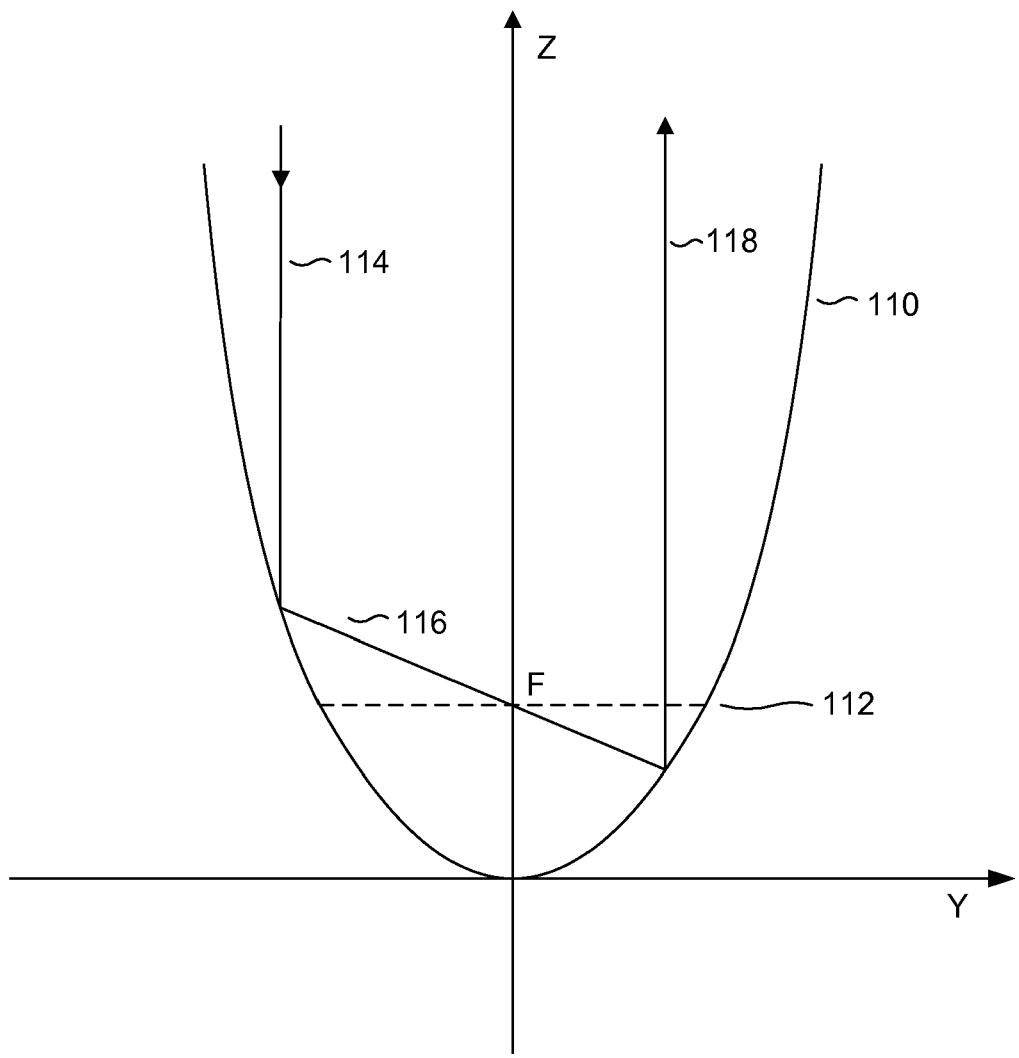
FIG. 1 is a two-dimensional conceptual illustration of a technology of the present invention.

Referring to FIG. 1, an underlying concept of the embodiments of the present invention is explained. Given a parabola 110 disposed on a y-axis and a z-axis, conceptually, the shape of the parabola can be described be a simple mathematical function, $z=ay^2$, where incoming rays parallel to the z-axis would intersect the z-axis at its focal point "F", where the focal point is at $(0, \tfrac{1}{4}a)$, and "a" is a constant. The incoming ray intersects the parabolic surface and it is redirected towards the focal point at the incident plane 112 (the plane that is perpendicular to the axis of symmetry and passes through the focal point, "F").

Here, as shown, the incidental incoming light ray 114 is parallel to the axis of symmetry. The ray hits the parabolic surface and the parabolic reflector, by virtue of its properties, directs the beam towards its focal point and intersects the z-axis at intersection point "F". After the intersection, the ray hits the parabolic surface again, and the parabolic surface re-directs the ray 118 back toward its incident direction parallel to the axis of symmetry. Due to the unique characteristic of the paraboloid, reflected ray will be always be parallel to the axis of symmetry if the incoming ray is parallel to the axis of symmetry.

Figure 2:
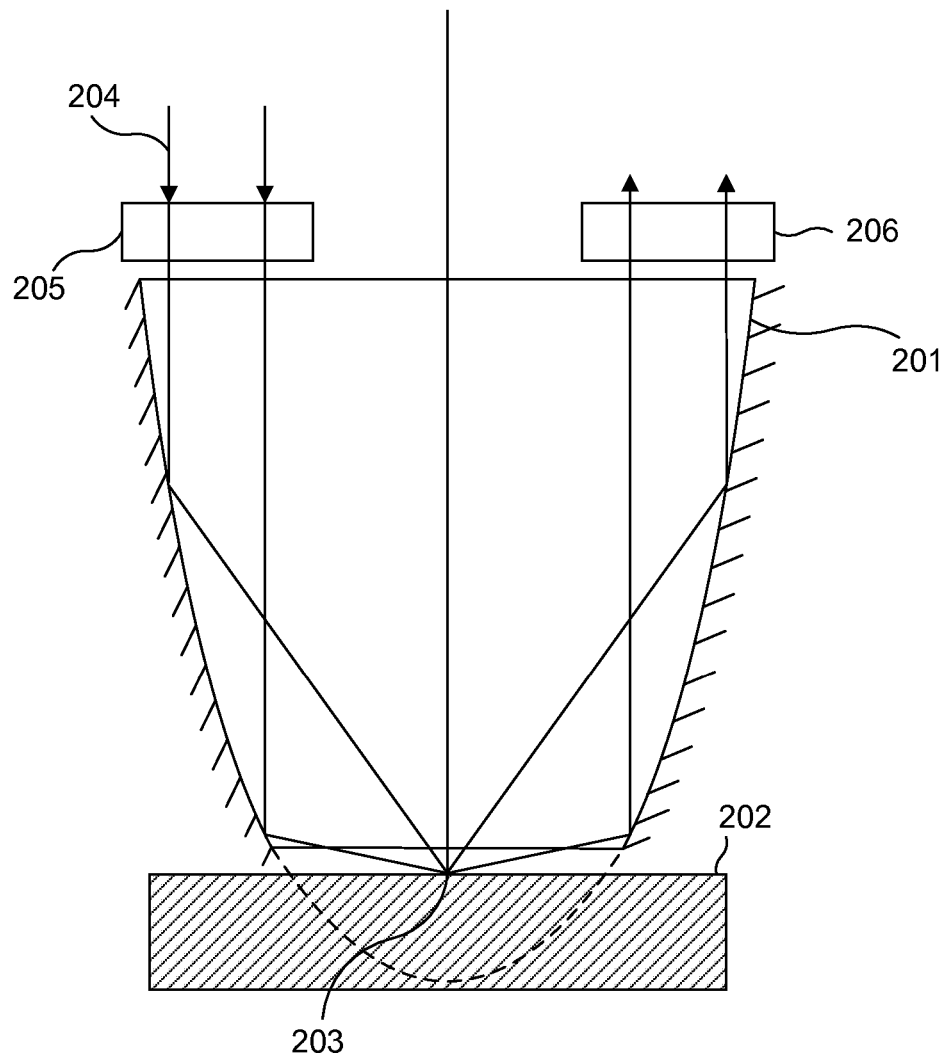
FIG. 2 is a side-view of a preferred embodiment of the present invention utilizing a parabolic reflector and a polarizer and a polarization analyzers.
Figure 3:
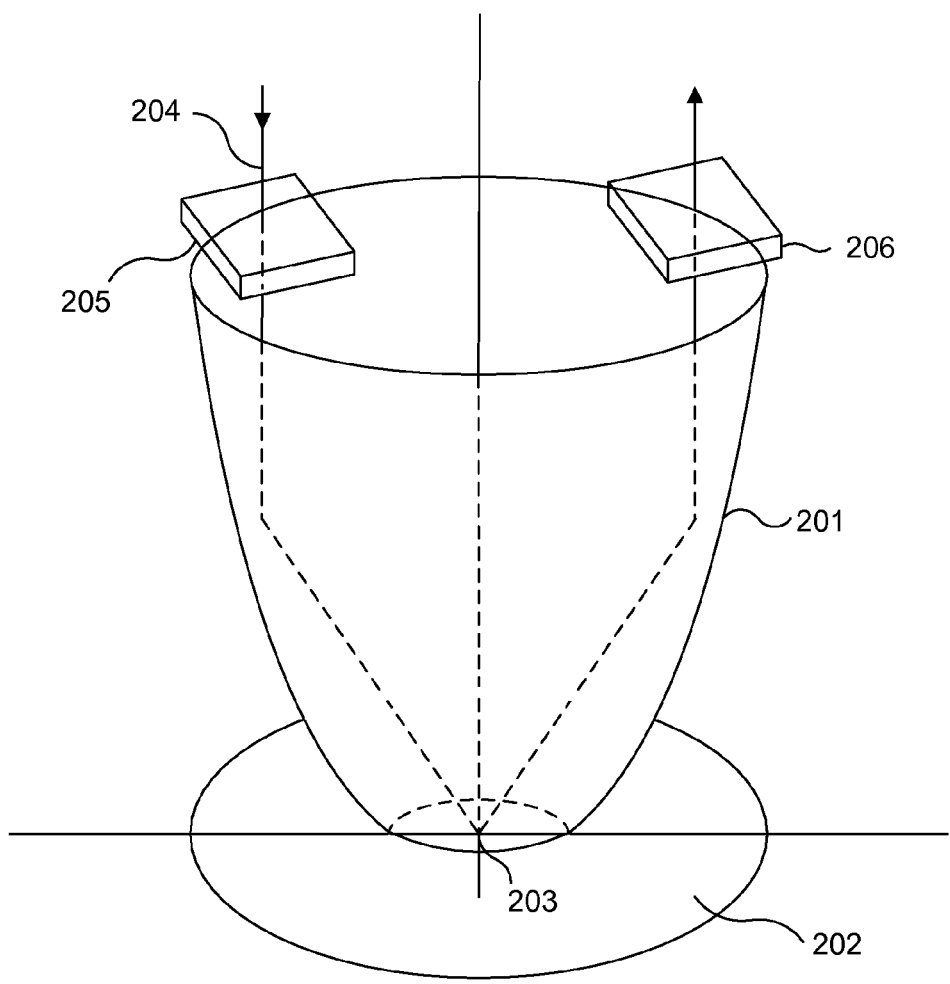
FIG. 3 is a top-angled view of a preferred embodiment of the present invention utilizing a parabolic reflector and a polarizer and an analyzers.

Referring to FIG. 2, a presently preferred embodiment of the present invention is disclosed. Here, a side view of an optical head is presented where the optical head comprising of a parabolic reflector 201 and a polarizer 205 and an analyzer 206. The parabolic reflector can be manufactured as a paraboloid and cut in such a manner such that its focal point 203 is at the surface of the object 202 to be measured or tested, the device-under-test ("DUT"). The function of the parabolic reflector 201 is to focus the incoming beam 204 to the surface of the DUT 202 at the focal point 203 and collects the reflected beam from the focal point 203. FIG. 3 illustrates a top-front view the parabolic reflector 201 with the polarizer 205 and analyzer 206 disposed at the opening of the parabolic reflector.

Figure 4:
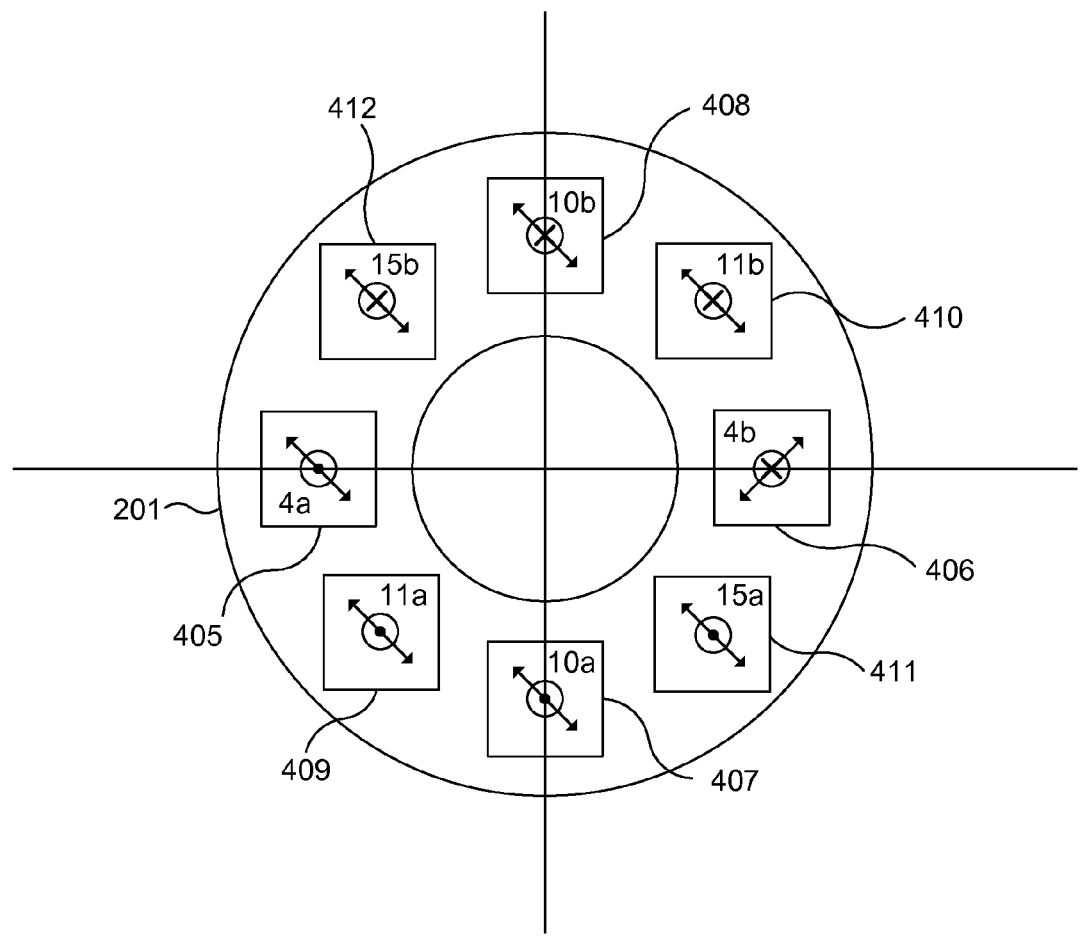
FIG. 4 is a top-view of a preferred embodiment of the present invention utilizing a parabolic reflector and a plurality of polarizers and analyzers.

In the preferred embodiment of the present invention, in performing ellipsometric measurements, several polarizers and analyzers are arranged in such a manner that Rp and Rs as well as the incident power of incoming beam can be measured simultaneously. FIG. 4 shows one of such arrangements in illustrating a top view of an optical head. Here, there are eight polarizers and analyzers, 405 and 406, 407 and 408, 409 and 410, and 411 and 412, for incoming rays and reflected rays. Their polarizing axes are parallel to each other except polarizer 406 whose axis is perpendicular to the rest. In following the illustrated four rays (4a/4b, 10a/10b, 11a/11b and 15a/15b), the principle of this device can be demonstrated. Here the letter "a" represents incoming rays and the letter "b" represents outgoing rays.

Each pair of the rays defines a plane of incidence. Ray 4a passes through polarizer 405 and becomes polarized along the direction of the arrow shown. This direction is perpendicular to the incident plane 201. After reflecting off the parabolic reflector and the focal point, the outgoing ray 4b passes through another polarizer 406. This ray is then received by a detector whose output is proportional to the intensity of the ray.

The principle can be further illustrated in more rigorous mathematical expression illustrated below. Let's use Jones representation for polarization.

Incident beam electrical field:

$$\vec{E}_0 = \begin{pmatrix} E_x \\ E_y \end{pmatrix}$$

Polarizer:

$$\vec{P} = \begin{pmatrix} 1 & 0 \\ 0 & 0 \end{pmatrix}$$

Parabolic reflector:

$$\vec{M} = \begin{pmatrix} R_p^M & 0 \\ 0 & R_s^M \end{pmatrix}$$

Sample:

$$\vec{S} = \begin{pmatrix} R_p^{sample} & 0 \\ 0 & R_s^{sample} \end{pmatrix}$$

Coordinate rotation matrix:

$$\vec{R}(\theta) = \begin{pmatrix} \cos(\theta) & \sin(\theta) \\ -\sin(\theta) & \cos(\theta) \end{pmatrix}$$

Analyzer:

$$\vec{A} = \begin{pmatrix} 1 & 0 \\ 0 & 0 \end{pmatrix}$$

The electrical field for reflected beam:

$$\vec{E}_D = \vec{R}^{-1}(A)\vec{A}\vec{R}(A)\vec{M}\vec{S}\vec{M}\vec{R}^{-1}(P)P\vec{R}(P)\vec{E}_0$$

where $\vec{R}(A)$ and $\vec{R}(P)$ are the rotation matrices for analyzer with angle A and polarizer with angle P. The angle is measured clockwise from the plane of incidence along the propagation of the ray.

The intensity on the detector is proportional to $$I_D = \vec{E}_D \cdot \vec{E}_D^*$$
$$= [\vec{R}^{-1}(A)\vec{A}\vec{R}(A)\vec{M}\vec{S}\vec{M}\vec{R}^{-1}(P)P\vec{R}(P)\vec{E}_0] +$$
$$[\vec{R}^{-1}(A)\vec{A}\vec{R}(A)\vec{M}\vec{S}\vec{M}\vec{R}^{-1}(P)P\vec{R}(P)\vec{E}_0]$$
$$= \vec{E}_0^+ \vec{R}(P)^+ \vec{P}\vec{R}(P)\vec{M}^+ \vec{S}^+ \vec{M}^+ \vec{R}(A)^+ \vec{A}\vec{R}(A)\vec{R}^{-1}(A)$$
$$\vec{A}\vec{R}(A)\vec{M}\vec{S}\vec{M}\vec{R}^{-1}(P)P\vec{R}(P)\vec{E}_0$$

It can be shown that $$I_D \propto \vec{E}_D \cdot \vec{E}_D^* =$$
$$|R_p|^2\cos^2 P + |R_s|^2\sin^2 P + [|R_p|^2\cos^2 P - |R_s|^2\sin^2 P]\cos(2A) +$$
$$2Re(R_p \cdot R_s)\sin P \cos P \sin(2A)$$

Here
$$R_p = R_p^{sample} R_p^M R_p^M$$
and
$$R_s = R_s^{sample} R_s^M R_s^M$$

For ray 4a and 4b,
A=45° and P=45°

$$I_1 = I_D \propto E_D \cdot E_D^* = \frac{1}{2}\{|R_p|^2 + |R_s|^2 + 2Re(R_p \cdot R_s^*)\}$$

For ray 10a and 10b,
A=−45° and P=45°

$$I_2 = I_D \propto E_D \cdot E_D^* = \frac{1}{2}\{|R_p|^2 + |R_s|^2 - 2\text{Re}(R_p \cdot R_s^*)\}$$

For ray 11a and 11b,
A=90° and P=90°

$$I_3 = I_D \propto E_D \cdot E_D^* = \frac{1}{2}\{|R_s|^2\}$$

For ray 15a and 15b,
A=0° and P=0°

$$I_4 = I_D \propto E_D \cdot E_D^* = \frac{1}{2}\{|R_p|^2\}$$

So $$\frac{I_2 - I_1}{I_2 + I_1} = \frac{2\text{Re}(R_p \cdot R_s^*)}{|R_p|^2 + |R_s|^2} = \frac{2\tan(\Psi)\cos(\Delta)}{1 + \tan^2(\Psi)}$$

and $$\frac{I_4}{I_3} = \frac{|R_p|^2}{|R_s|^2} = \tan^2(\Psi)$$

So, $$\tan(\Psi) = [\tan(\Psi)]_{Sample}\{\tan(\Psi)_{Mirror}\}^2 = \sqrt{\frac{I_4}{I_3}}$$

and $$\cos(\Delta) = \cos(\Delta_{Sample} + 2\Delta_{Mirror}) = \frac{1}{2} \cdot \left(1 + \frac{I_4}{I_3}\right)\left(\frac{I_2 - I_1}{I_2 + I_1}\right) \cdot \sqrt{\frac{I_3}{I_4}}$$

The mirror effect can be calibrated out with a known quantity sample.

Figure 5:
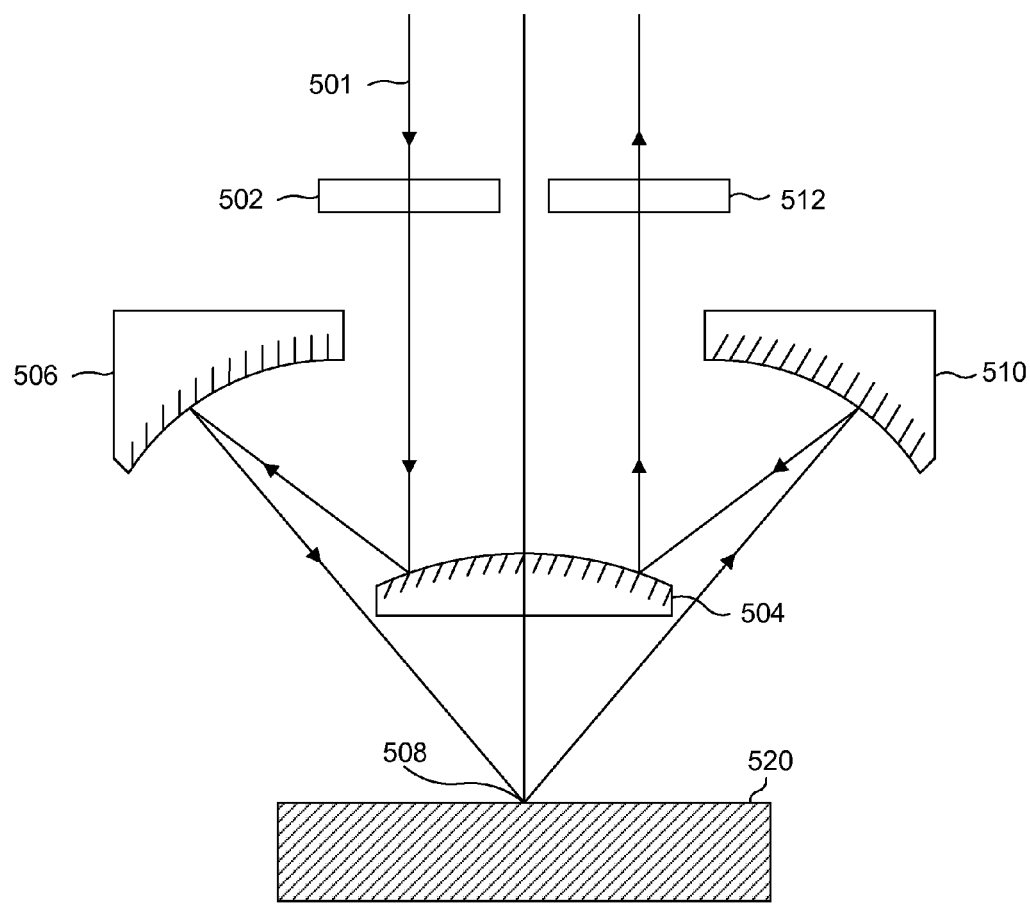
FIG. 5 is a side view of an alternative embodiment of the present invention using a different reflector.
Figure 6:
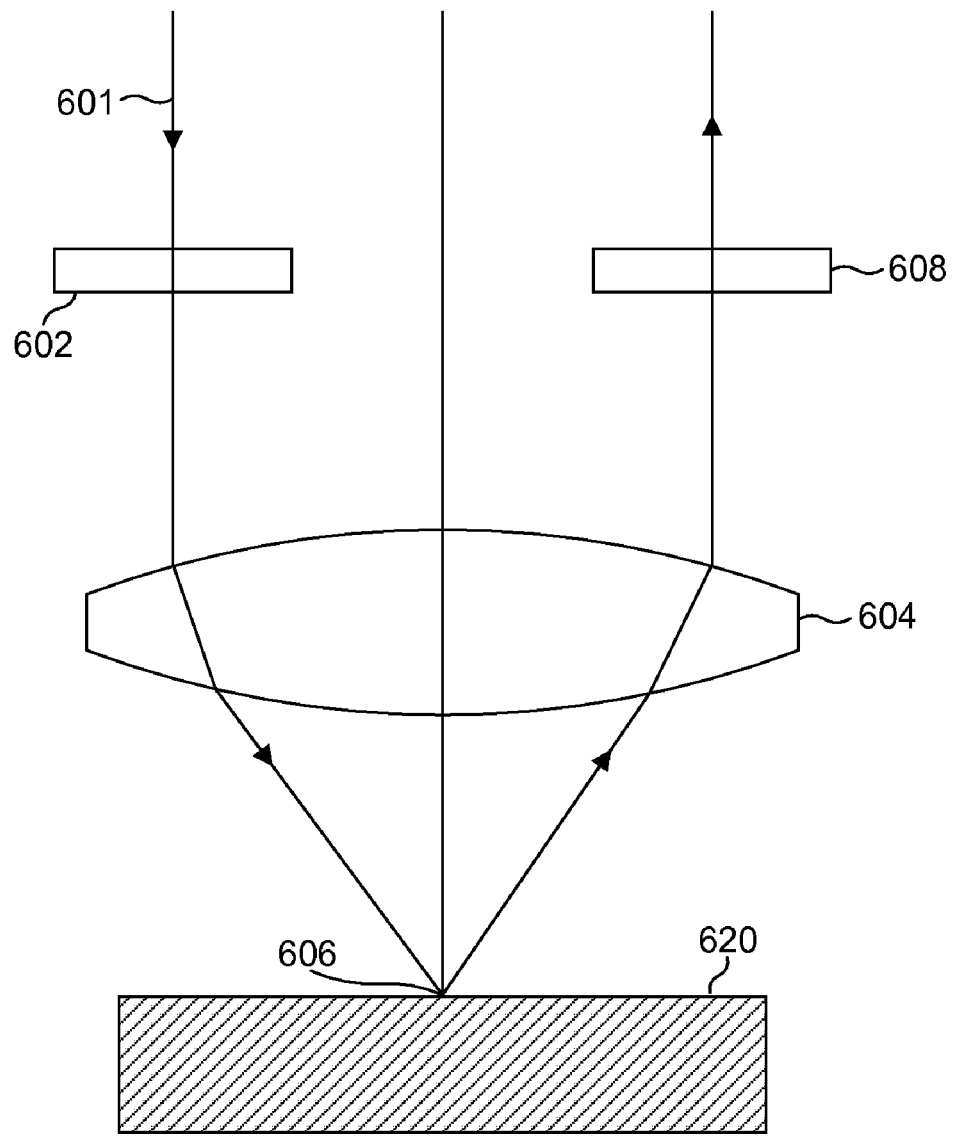
FIG. 6 is a side view of yet another alternative embodiment of the present invention using a different reflector.

Other reflecting optics can also be used to realize the ellipsometric measurements, such as those illustrated in FIG. 5 and FIG. 6. In FIG. 5, an incoming ray passes through a polarizer 502, reflects off a lens disposed at 504 and another lens at 506 to focal on a focal point at 403 and a DUT 520. After reflecting off the DUT 520, the ray reflects off lens at 510 and lens at 504 to pass through an analyzer 512. In FIG. 6, an incoming ray 601 passes through a polarizer 602, passes through a lens 604 and focuses at focal point 606 and a DUT 620. The ray reflects off the DUT, passes back through the lens 604 and an analyzer 608. Note that polarization analyzers can be used, where a polarization analyzer redirects incoming light into two orthogonally polarized directions.

Figure 7:
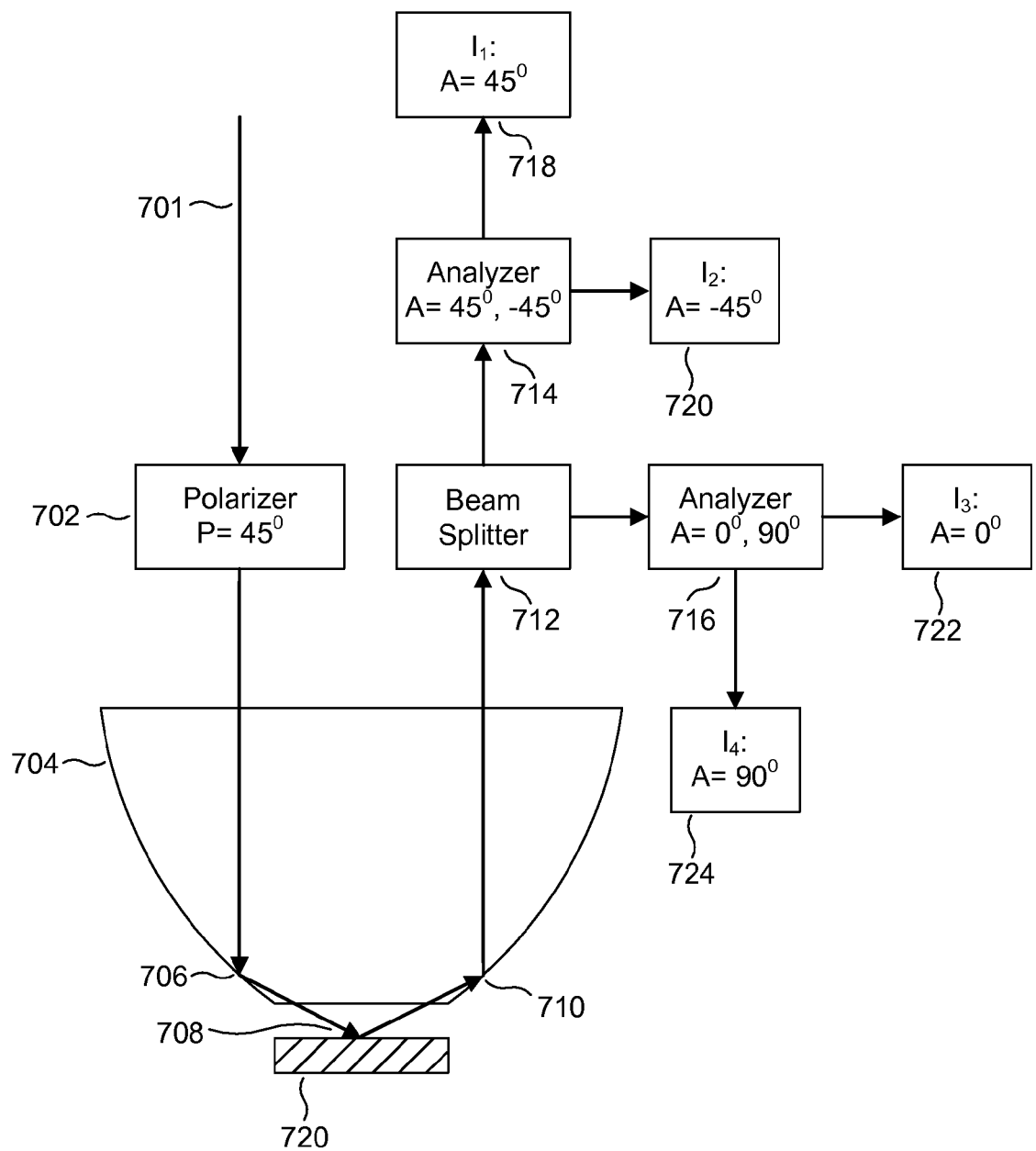
FIG. 7 is another embodiment of the present invention where a beam splitter is used to direct light rays to different analyzers.

FIG. 7 illustrates an alternative embodiment where the incident ray is linearly polarized at P=45°, and four analyzers are arranged at A=45°, −45°, 0°, and 90°. There is the incident ray 701 passing through a polarizer for P=45° 702, which can be any lens or a parabolic mirror, reflecting off a parabolic reflector 704 at 706 to focus at focal point 708, and reflecting off a device-under-test 720. The reflected ray again reflects off the parabolic reflector 704 at 710, passes to a beam splitter 712 to split off to a first analyzer for A=45° and −45° 714 and a second analyzer for A=0° and 90° 716.

Here, for A=45° and P=45° 718

$$I_1 = I_D \propto E_D \cdot E_D^* = \frac{1}{2}\{|R_p|^2 + |R_s|^2 + 2\text{Re}(R_p \cdot R_s^*)\};$$

for A=−45° and P=45° 720

$$I_2 = I_D \propto E_D \cdot E_D^* = \frac{1}{2}\{|R_p|^2 + |R_s|^2 - 2\text{Re}(R_p \cdot R_s^*)\};$$

for A=90° and P=45° 724

$$I_3 = I_D \propto E_D \cdot E_D^* = \frac{1}{2}\{|R_s|^2\};$$

and for A=0° and P=45° 722

$$I_4 = I_D \propto E_D \cdot E_D^* = \frac{1}{2}\{|R_p|^2\}.$$

So, $$\frac{I_2 - I_1}{I_2 + I_1} = \frac{2\text{Re}(R_p \cdot R_s^*)}{|R_p|^2 + |R_s|^2} = \frac{2\tan(\Psi)\cos(\Delta)}{1 + \tan^2(\Psi)}$$

and $$\frac{I_4}{I_3} = \frac{|R_p|^2}{|R_s|^2} = \tan^2(\Psi).$$

So, $$\tan(\Psi) = [\tan(\Psi)]_{Sample}\{\tan(\Psi)_{Mirror}\}^2 = \sqrt{\frac{I_4}{I_3}}$$

and $$\cos(\Delta) = \cos(\Delta_{Sample} + 2\Delta_{Mirror}) = \frac{1}{2} \cdot \left(1 + \frac{I_4}{I_3}\right)\left(\frac{I_2 - I_1}{I_2 + I_1}\right) \cdot \frac{I_3}{I_4}.$$

Figure 8:
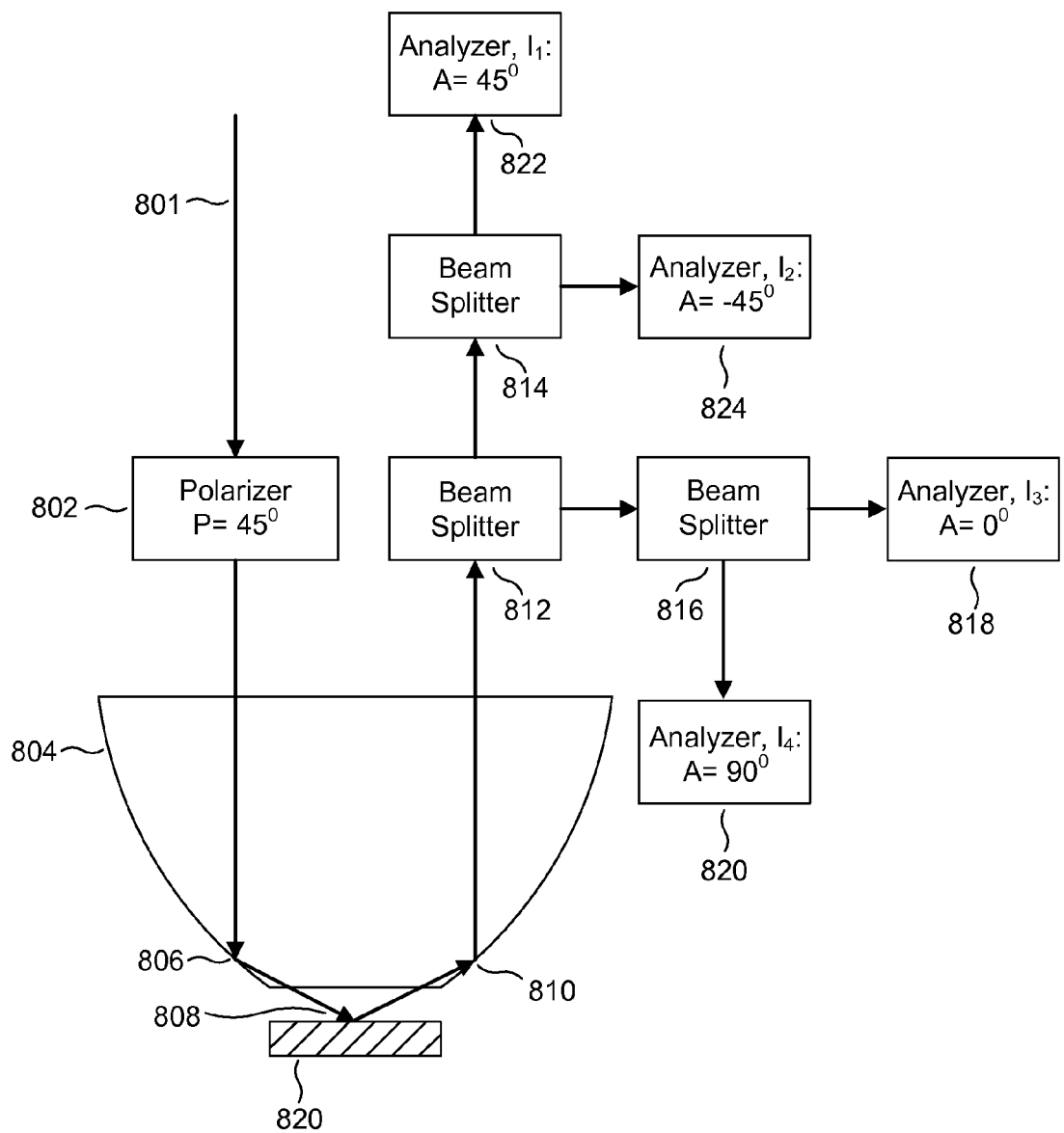
FIG. 8 is another embodiment of the present invention where beam splitters are used to direct light rays to different analyzers.

FIG. 8 illustrates yet another alternative embodiment where the incident ray is linearly polarized at P=45°, and four analyzers are arranged at A=45°, −45°, 0°, and 90°. There is the incident ray 801 passing through a polarizer for P=45° 802, which can be any lens or a parabolic mirror, reflecting off a parabolic reflector 804 at 806 to focus at focal point 808, and reflecting off a device-under-test 820. The reflected ray again reflects off the parabolic reflector 804 at 810, passes to a first beam splitter 812 to split off to a second beam splitter 814 and a third beam splitter 816. From the first beam splitter, the ray passes to analyzers for A=45° 822 and A=−45° 824; and from the second beam splitter 816, the ray passes to analyzers for A=0° 818 and A=90° 820.

While the present invention has been described with reference to certain preferred embodiments, it is to be understood that the present invention is not limited to such specific embodiments. Rather, it is the inventor's contention that the invention be understood and construed in its broadest meaning as reflected by the following claims. Thus, these claims are to be understood as incorporating not only the preferred embodiments described herein but all those other and further alterations and modifications as would be apparent to those of ordinary skilled in the art.

We claim:

1. A method for extracting ellipsometric information of a device-under-test for an ellipsometer, comprising the steps:
   providing simultaneously a plurality of incoming polarized beams;
   using an optical focusing device to focus said plurality of incoming polarized beams on a spot on a DUT, wherein the polarized beams have the same angle of incidence;
   collecting simultaneously a plurality of beams specularly reflected from said DUT by said optical focusing device, wherein the specularly reflected beams have the same angle of reflection; and
   analyzing said collected beams using a plurality of analyzers.

2. The method of claim 1 wherein polarizers are used in providing the polarized beams and wherein the polarized beams are polarized at different designated polarizing angles.

3. The method of claim 2 wherein the analyzing step is performed with a plurality of analyzers, each having a designated polarizing angle with respect to its respective polarizer.

4. A method for extracting ellipsometric information for an ellipsometer, comprising the steps of:
   providing an incoming polarized beam having a first polarization angle;
   using a parabolic reflector to focus said incoming polarized beam on a spot on a DUT;
   collecting said beam specularly reflected from said DUT by said parabolic reflector;
   splitting said collected beam to a first analyzer and a second analyzer for analyzing the split beams, each of said split beams having an analyzer angle, wherein the split beams are polarized at different designated polarizing angles; and
   analyzing said split beams to extract information using a plurality of analyzers.

5. The method of claim 4 wherein in the splitting step, the collected beam is split and directed to four analyzers, each having a designated polarizing angle.

6. A method for extracting ellipsometric information of a device-under-test for an ellipsometer, comprising the steps:
   providing simultaneously a plurality of incoming polarized beams using a plurality of polarizers, wherein polarizers are used in providing the incoming polarized beams, wherein the incoming polarized beams are polarized at different designated polarizing angles, and wherein the polarized beams have the same angle of incidence;
   using a parabolic reflector to focus said plurality of incoming polarized beams on a spot on a DUT;
   using a parabolic reflector to simultaneously collect a plurality of beams specularly reflected from said DUT, wherein the specularly reflected beams have the same angle of reflection; and
   analyzing said collected beams using a plurality of analyzers, wherein the analyzers polarize the specularly reflected beams and wherein the specularly reflected beams are polarized at different designated polarizing angles.

7. The method of claim 1 wherein the optical focusing device is a parabolic reflector.

8. The method of claim 1 wherein the optical focusing device is a lens.

9. The method of claim 3 wherein the analyzers polarize the specularly reflected beams and wherein the specularly reflected beams are polarized at different designated polarizing angles.

10. The method of claim 9 wherein the polarized incoming beams that enter the optical focusing device and the polarized reflected beams that exit the optical focusing device are equidistant from the axis of symmetry of the optical focusing device.

11. The method of claim 1 wherein there is a plurality of incoming beams that enter the optical focusing device (having an axis of symmetry) and the same number of reflected beams that exit the optical focusing device, wherein the beams are distributed equal distance from the center of the axis of symmetry and wherein the beams are distributed evenly around the axis of symmetry such that each of the beams is equal distance from its two immediate adjacent beams.

12. The method of claim 3 wherein the polarizers and the analyzers each have a polarizing axis and wherein a plurality of the polarizing axes of the polarizers and analyzers are in parallel.

13. The method of claim 4 wherein a polarizer is used in providing the polarized beam.

14. The method of claim 6 wherein the polarized incoming beams that enter the parabolic reflector and the polarized reflected beams that exit the parabolic reflector are equidistant from the axis of symmetry of the parabolic reflector.

15. The method of claim 6 wherein the polarizers and the analyzers each have a polarizing axis and wherein a plurality of the polarizing axes of the polarizers and analyzers are in parallel.

16. The method of claim 6 wherein there is a plurality of incoming beams that enter the parabolic reflector (having an axis of symmetry) and the same number of reflected beams that exit the parabolic reflector, wherein the beams are distributed equal distance from the center of the axis of symmetry and wherein the beams are distributed evenly around the axis of symmetry such that each of the beams is equal distance from its two immediate adjacent beams.

* * * * *